(12) United States Patent
McFadden et al.

(10) Patent No.: US 8,181,324 B2
(45) Date of Patent: May 22, 2012

(54) CATHETER WITH KNIT SECTION

(75) Inventors: Jill M. McFadden, Townsend, MA (US); Earl Bardsley, Newton, MA (US); Robert Garabedian, West Townsend, MA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

(21) Appl. No.: 12/906,872

(22) Filed: Oct. 18, 2010

(65) Prior Publication Data
US 2011/0024025 A1   Feb. 3, 2011

Related U.S. Application Data

(63) Continuation of application No. 09/097,023, filed on Jun. 12, 1998, now Pat. No. 7,815,626.

(51) Int. Cl.
*B23P 17/00* (2006.01)
*B29C 70/10* (2006.01)

(52) U.S. Cl. ...................... 29/419.1; 156/149

(58) Field of Classification Search ............ 29/428, 29/419.1, 435, 434, 436, 450, 458, 469, 506, 29/508; 156/149; 604/280, 282, 264, 523–527; 600/585
See application file for complete search history.

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 3,753,700 A | 8/1973 | Harrison et al. |
| 3,945,052 A | 3/1976 | Liebig |
| 3,996,938 A | 12/1976 | Clark, III |
| 4,571,240 A | 2/1986 | Samson et al. |
| 4,637,396 A | 1/1987 | Cook |
| 4,655,771 A | 4/1987 | Wallsten |
| 4,739,768 A | 4/1988 | Engelson |
| 4,767,400 A | 8/1988 | Miller et al. |
| 4,873,983 A | 10/1989 | Winters |
| 4,898,591 A | 2/1990 | Jang et al. |
| 4,922,905 A | 5/1990 | Strecker |
| 5,257,974 A | 11/1993 | Cox |
| 5,338,295 A | 8/1994 | Cornelius et al. |
| 5,356,388 A | 10/1994 | Sepetka et al. |
| 5,370,660 A | 12/1994 | Weinstein et al. |
| 5,415,634 A | 5/1995 | Glynn et al. |
| 5,429,597 A | 7/1995 | DeMello et al. |
| 5,443,449 A | 8/1995 | Buelna |
| 5,462,523 A | 10/1995 | Samson et al. |
| 5,480,423 A | 1/1996 | Ravenscroft et al. |
| 5,533,985 A | 7/1996 | Wang |
| 5,540,707 A | 7/1996 | Ressemann et al. |
| 5,549,109 A | 8/1996 | Samson et al. |

(Continued)

FOREIGN PATENT DOCUMENTS

| | | |
|---|---|---|
| JP | 2723223 | 11/1988 |
| JP | 5220225 | 8/1993 |

*Primary Examiner* — John C Hong
(74) *Attorney, Agent, or Firm* — Seager, Tufte & Wickhem, LLC

(57) ABSTRACT

A catheter section comprising an elongate tubular member having a proximal end, a distal end, and a passageway defining a lumen extending between the proximal and distal ends. The elongate tubular member includes a knit tubular member and an inner tubular liner in coaxial relationship with the knit tubular member. The catheter section is for use as a distal section in a catheter having a relatively stiff proximal section.

19 Claims, 4 Drawing Sheets

U.S. PATENT DOCUMENTS

| | | |
|---|---|---|
| 5,599,296 A | 2/1997 | Spears |
| 5,653,684 A | 8/1997 | Laptewicz |
| 5,662,713 A | 9/1997 | Andersen et al. |
| 5,674,276 A | 10/1997 | Andersen et al. |
| 5,702,373 A | 12/1997 | Samson |
| 5,772,681 A | 6/1998 | Leoni |

CATHETER WITH KNIT SECTION

RELATED APPLICATIONS

This application is a continuation of U.S. application Ser. No. 09/097,023, filed Jun. 12, 1998, now U.S. Pat. No. 7,815,626, the entire disclosure of which is incorporated herein by reference.

FIELD OF THE INVENTION

This invention relates generally to catheters, and more particularly, to a catheter having a knit section.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of diseases of the circulatory system is via angioplasty (PCA). Such a procedure uses catheters having balloons on their distal tips. It is similarly common that those catheters are used to deliver a radiopaque agent to the site in question prior to the PCA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. U.S. Pat. No. 5,702,373 discloses another catheter design for use in accessing a tissue target within the body. The catheter includes a braided reinforcing member for high kink resistance.

These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered.

This invention is an adaptable one and may be used in a variety of catheter formats. The invention utilizes the concept of combining one or polymeric tubes with a knit tube. The construction technique has the benefit of producing catheter sections having small overall diameters but with exceptional strength, resistance to ovalization and kinking, and recovery from kinking (even in vivo) should such kinking occur. The catheter may be used in conjunction with a guidewire, but the catheter may also be used as a flow-directed catheter with the attachment of a balloon or in combination with a specifically flexible tip.

Knit tubular members have been used in surgical devices such as stents. For example, U.S. Pat. No. 5,662,713 discloses a self-expanding stent formed by knitting a wire into a pattern of overlapping loops. The stent is placed within the body to perform a function such as maintaining open a body lumen. U.S. Pat. No. 5,480,423 discloses a self-expanding knit stent and a catheter for delivering the stent.

None of the documents cited above provides a catheter structure described in the specification and set forth in the claims recited below, particularly when the flexibility and ability to resist kinks is factored into the physical description of the devices.

SUMMARY OF THE INVENTION

This invention is a catheter section having a knit tubular member. The catheter section may include an inner tubular liner in coaxial relationship with the knit tubular member and an outer tubular cover surrounding the knit tubular member. The knit tubular member may comprise a metal alloy, polymeric material or other suitable material.

The catheter section may be used as a distal segment of a catheter with a relatively more stiff proximal segment. The proximal segment may also include an inner liner and outer cover. A stiffener formed from a knit member, braid, or coil may also be interposed between the inner liner and outer cover.

The kink resistance of the catheter is due to the presence of the knit tubular member. In addition to exceptional kink resistance, the catheter section may be made in such a way that the wall is extraordinarily thin, particularly when compared to walls of catheters having equal strength but made solely of polymeric materials. The catheter section additionally is very resilient in that, should the catheter section be kinked, the kink is self-healing. This resiliency means that the catheter need not be withdrawn from a patient's vasculature simply because the catheter has inadvertently kinked. Simple movement of the catheter will cure the kink. Kinking minimization is a matter of concern with many catheters in the marketplace today. The knit tubular member also minimizes circumferential collapse (ovaling of the catheter section) and increases the burst strength of the catheter section.

The catheter assembly may also have ancillary components such as a luer lock and some manner of providing radiopacity.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DESCRIPTION OF THE INVENTION

This invention is a catheter assembly having a more distal segment preferably made up of an inner liner, an outer covering, and a knitted layer located between the liner and the covering, and a more proximal segment comprising, for example, a stiff polymeric or metallic tubing member. Other sections of these or other designs may be placed variously between the noted sections or distal of the distal knitted section noted above.

Figure 1:
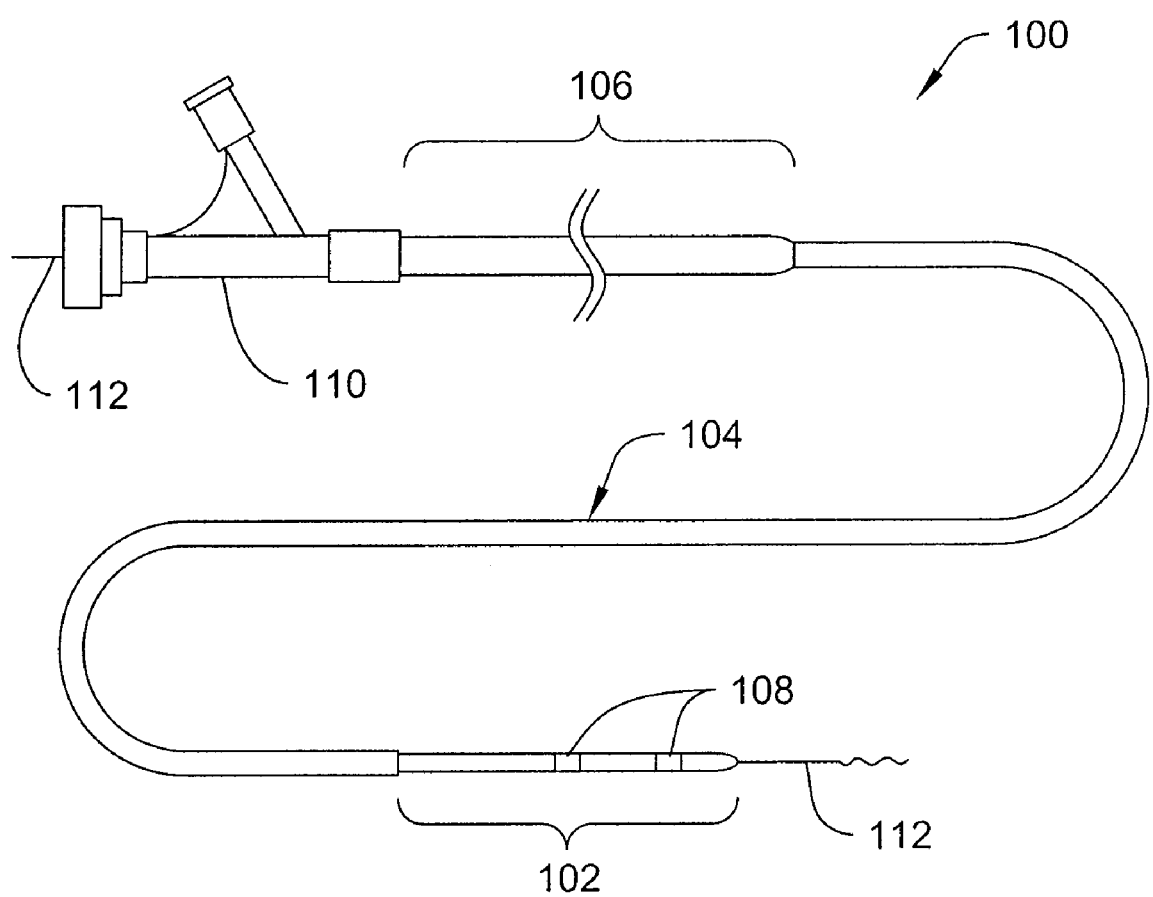
FIG. 1 is a side view of a typical three section catheter made using the concepts of this invention.

A typical multi-section catheter 100 which may incorporate the concepts of this invention is shown in FIG. 1. Such a catheter is described in more detail in U.S. Pat. No. 4,739,768, to Engelson, the entirety of which is incorporated by reference and is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever smaller vascular areas. This smaller diameter requires a concomitant thinning of the wall section. The thinner section walls may kink or ripple when actively pushed along the guidewire or when vaso-occlusive devices are pushed through the catheter's lumen. The typical configuration shown in FIG. 1 has a distal section 102 having significant flexibility, an intermediate section 104 which is typically less flexible, and a long proximal section 106 which in turn is least flexible. The distal section 102 is flexible and soft to allow deep penetration of the extraordinary convolutions of the neurological vasculature without trauma. Various known and often necessary accessories to the catheter assembly, e.g., one or more radiopaque bands 108 at the distal region to allow viewing of the position of the distal region under fluoroscopy and a luer assembly 110 for guidewire 112 and fluids access, are also shown in FIG. 1. The typical dimensions of this catheter are:

| | |
|---|---|
| Overall length: | 60-200 cm |
| Proximal Section (106): | 30-150 cm |
| Intermediate Section (104): | 20-50 cm |
| Distal Section (102): | 2.5-30 cm |

Obviously, these dimensions are not particularly critical to this invention and are selected as a function of the malady treated and its site within the body. Typical of the catheters made using this invention are those in the 2 French to 8 French range (1 French=0.013 inch). The inner diameter of such catheters is then 10 mils, to 91 mils. (1 mil=0.001 inch).

Furthermore, a catheter made using this inventive concept need not be of three sections with increasing stiffness as is shown in FIG. 1. The catheter may be of two discrete sections or may be of four or more discrete sections of differing flexibility. Through judicious choice of physical parameters for the catheter sections, the components may also have varying physical parameters (e.g., lubricity, flexibility, wall thickness, inner or outer layer member composition, etc.) within the sections. Typically, although not necessarily, when a three section catheter is desired, the most proximal section 106 is the "more proximal" or "stiff" section described herein. Again, although not necessarily, when a three section catheter is desired, the most distal section 102 is the "more distal" or "flexible" (soft) section.

Figure 2:
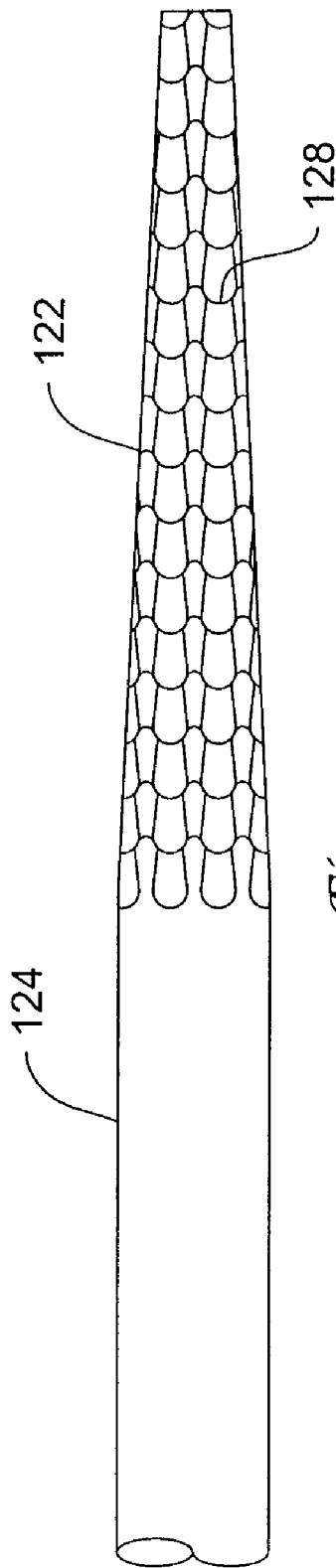
FIG. 2 is an enlarged view of a portion of the catheter of FIG. 1.

FIG. 2 shows one variation of a distal segment 122 having a knit tubular member 128, and a more proximal segment 124 of a catheter. As previously discussed, the more proximal segment 124 is stiffer than the distal segment 122. The knit tubular member 128 may also extend into the more proximal segment 124.

Figure 3:
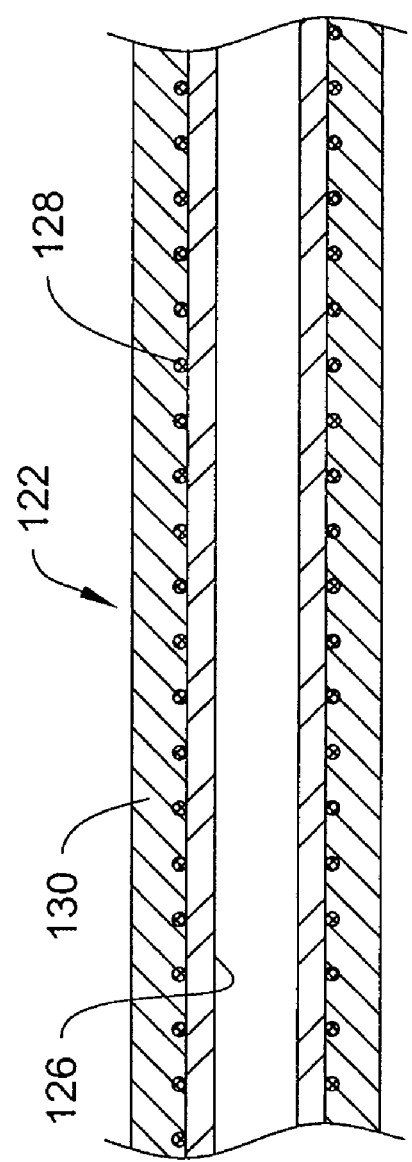
FIG. 3 is a side view of a distal section of the catheter of FIG. 1.

FIG. 3 shows an enlarged view of the more distal segment 122 with an outer tubular cover 130 extending over the knit tubular member 128. The knit member 128 is interposed between the outer cover 130 and an inner tubular liner 126. Both the inner liner 126 and the outer cover 130 are preferably polymeric and may be melt-miscible. The materials of the inner and outer layers 126, 130 may also contain adhesives. The outer cover 130 is preferably heat-shrunk, extruded, or bonded onto the inner liner 126 and knit member 128 as further described below.

Preferred polymeric materials for the inner liner 126 include fluoropolymers including PTFE, FEP, vinylidene fluoride, polyethylene, polyvinyl chloride (PVC), ethyl vinyl acetate (EVA), polyethylene terephthalate (PET), Pebax (polyether block amide), Nylon, and their mixtures, alloys, copolymers and block copolymers. Another useful class of polymers is thermoplastic elastomers, including those containing polyesters as components. Typical of this class is HYTREL. The inner liner 126 may be coated onto the inner surface of the knit member 128. Polyesters and polyimides, in particular, are useful as adhesives in this service. The inner liner 126 may also be formed by dipping a mandrel into a molten polymer, for example. The wall thickness of the inner liner 126 may be between 0.3 mils, and 3.0 mils., for example.

The outer cover 130 may be made of polyethylene or of EVA or their mixtures, for example. Preferred polymeric materials for the outer cover 130 include polyimide, polyamide, polypropylene, fluoropolymers including PTFE, FEP, Pebax, Nylon, vinylidene fluoride, and their mixtures, alloys, copolymers, and block copolymers. The polymer is typically extruded onto a tubing of appropriate size and thickness and then crosslinked to raise the melt temperature of the resulting tubing. The tubing is then inflated and perhaps stretched to give the included polymer a specific molecular orientation. The tubing, so treated, may then be slipped over the combination of inner liner 126 and knit member 128 and heat shrunk into place. If a section with even more flexibility is required, the outer cover 130 may also be of a member selected from a more flexible material such as polyurethane, low density polyethylene (LDPE), polyvinylchloride, THV, and other polymers of suitable softness or modulus of elasticity. The wall thickness of the outer cover 130 may be between 0.5 mils, and 10 mils., for example.

It is to be understood that the materials and thickness of the inner liner 126 and outer cover 130 may be different than described herein without departing from the scope of the invention. Furthermore, each of the polymers noted herein may be used in conjunction with radiopaque filler materials such as barium sulfate, bismuth trioxide, bismuth carbonate, powdered tungsten, powdered tantalum, or the like so that the location of various portions of the catheter sections may be radiographically visualized within the human body.

The knit tubular member 128 is preferably formed from a metal alloy, such as stainless steel, tantalum or its alloys, tungsten, platinum, or a superelastic alloy. Preferred superelastic alloys include the class of nickel/titanium materials known as nitinol, disclosed in U.S. Pat. Nos. 3,174,851, 3,351,463, and 3,753,700. Commercial alloys containing up to about 5% of one or more other members of the iron group, e.g., Fe, Cr, Co, are considered to be encompassed within the class of superelastic nickel/titanium alloys suitable for use. When using a superelastic alloy, an additional heat treat step may be desirable to preserve the shape of the knit tubular member 128. After heat treatment, the knit member 128 retains its shape and the alloy retains its superelastic properties.

The knit member 128 may also be formed from a non-metal alloy such as carbon/graphite, aramids (e.g., Kevlar, Tehnora, Twaron), liquid crystal polymer (LCP) (e.g., Vectran, PBO), polyethylene (e.g., Spectra, Dyneema, Certran), polyester (e.g., Dacron, Pentex, Dacronr), or Nylon.

Figure 4:
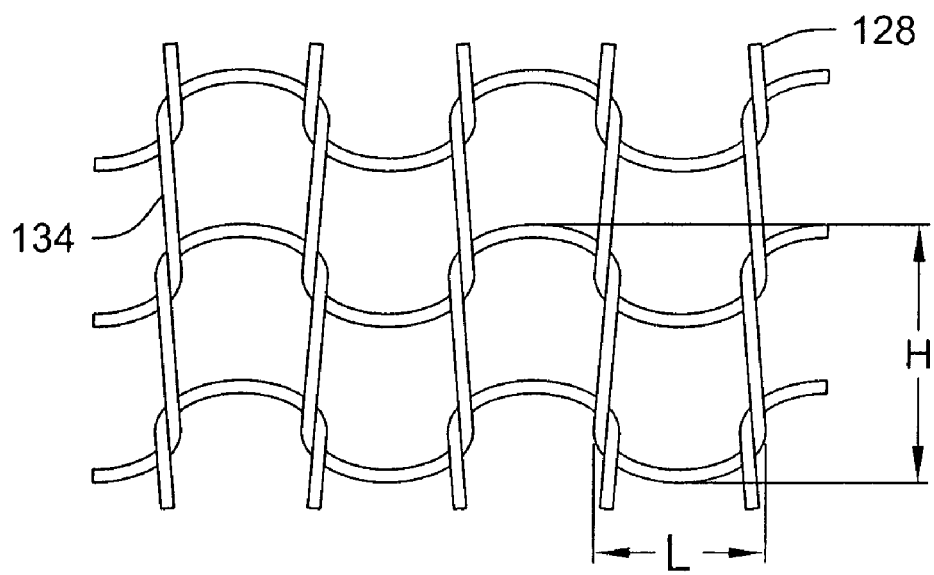
FIG. 4 is an enlarged partial view of a knit tubular member of the catheter of FIG. 1.

FIG. 4 shows a front half of the knit tubular member 128. The knit member 128 is preferably formed from a wire 134 having a generally circular cross-sectional shape. The diameter of the wire is preferably about 0.3 mil.-1.5 mil. The loop length L of the knit may be about 3.0 mil.-15.0 mil., and the peak-to-peak height H of the loops may be about 3.0 mil.-30.0 mil., for example. The wire may have other cross-sectional shapes such as rectangular (i.e., ribbon), for example. The knit tubular member 128 is preferably knitted from a single strand and configured with the "down loops" and "up loops" having the same size. Multiple strands or other knit configurations may also be used. For example, multiple strands of the same or different material may be knit together (i.e., co-knit), as is well known by those skilled in the art. The knit member 128 may also be formed from a multifilament wire comprising stainless steel, platinum, nitinol, or any combination of these or other materials. For example, the multifilament wire may comprise stainless steel and platinum, or nitinol and platinum.

The knit member 128 is preferably tightly knitted so that it is not significantly radially expandable (e.g., does not increase in diameter more than about 5% when an outwardly directed radial force is applied to an inner surface of the knit member).

The knit member 128 may be knitted on a conventional knitting machine, such as an Emilnestle machine, (product designation number E88-187, or E90-102). The knitting machine produces a long rope of knit loops (FIG. 4). After knitting, the tubular member 128 may be mounted on a mandrel for annealing, to relieve strains induced by the plastic deformation of knitting and to produce greater elasticity in the wire 134, if a superelastic alloy is used, for example. After annealing, the member 128 is cut to its final length. The knit member may also be formed directly on the inner liner 126. To prevent the knit member 128 from unraveling, the last three loops may be coated or the outer cover may be used to prevent unraveling. The sharp ends of the wire 134 are covered by the outer cover 130.

The number and type of sections of the catheter may vary. The catheter sections may have multiple polymeric layers exterior of the knit member 128 as well as multiple polymeric liner members interior to the knit member. The catheter sections may also include multiple layers of knit members 128 between or amongst the various polymer layers. Each individual section of the catheter may also vary in stiffness. Different sections may be connected together by soldering or with an adhesive, for example. An outer cover, as described above, may also be applied to the outer surface of both the more distal segment 122 and the more proximal segment 124 to connect the two sections together. The outer cover of the proximal and distal sections may also be formed as interlocking components. For example, adjacent sides of the outer covers may have opposing interlocking teeth or wedge shaped members which fit together to connect two sections with a smooth transition. The outer cover may be a material of suitable flexibility and compatibility such as a polyurethane, low density polyethylene, Pebax, or Nylon. The exterior and interior surfaces of the catheter or catheter section may be coated with a lubricious layer such as a hydrophilic polymer layer, which is either chemically bonded to the layer or is physically coated on the surface.

The inner liner 126 may be omitted, particularly in the more proximal segment 124 since the majority of materials which are suitable for the more proximal segment 124 are very hard and suitably slippery for passage of guidewires and the like. The more proximal segment 124 may be a simple tubular member comprising unfilled, filled, or fiber-reinforced, tough, polymeric materials preferably having high flexural moduli. Examples include polyamides, polyamide-polyimides, polyimides (thermoset and thermoplastic), polycarbonates, LCP's, and acetals, for example. To integrate the more proximal section of the catheter assembly with materials found in adjacent sections, the choice of materials for the proximal section is desirably a polyamide which is melt-miscible with a polymeric component found in the adjacent more distal section. The distal section may have a covering of polyurethane, a block copolymer of a polyether and a polyamide (e.g., Pebax), or a low durometer Nylon.

Figure 5:
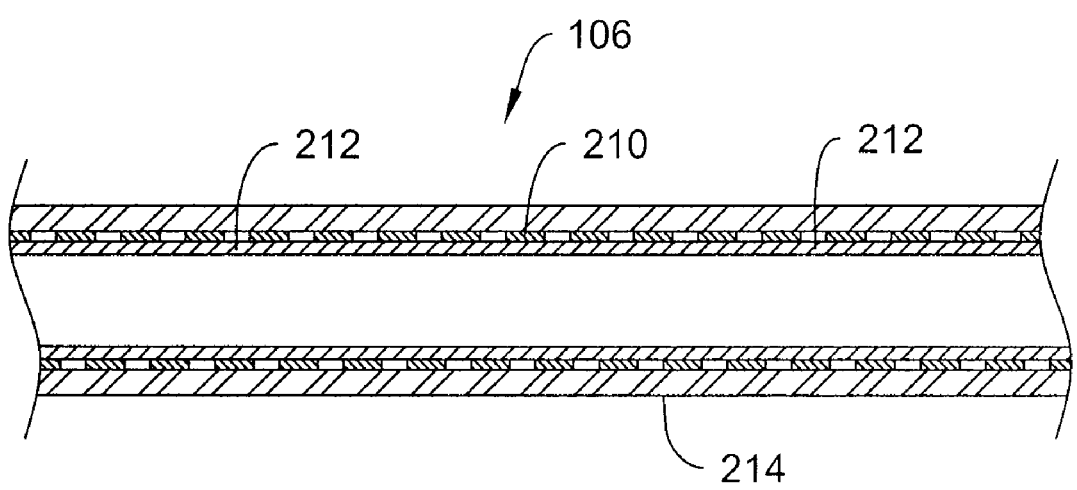
FIGS. 5 and 6 are cross-sectional views of a proximal section of alternate embodiments of the catheter of FIG. 1.
Figure 6:
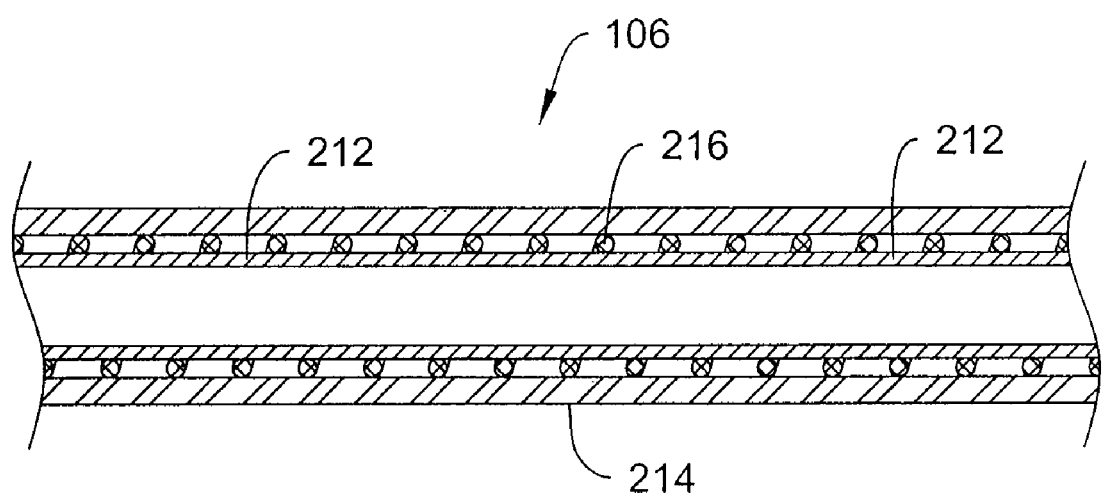

The proximal segment 124 may also comprise a stiffener interposed between an inner liner and an outer cover. The inner liner and outer cover may comprise the materials specified herein for the inner liner 126 and outer cover 130 of the distal segment 122. The outer cover and inner liner of the proximal section may be formed from the same material as the outer cover and inner liner of the distal section, or from different materials. The stiffener may be a knit, braided or coil member comprising a metal alloy such as nitinol or stainless steel, or a polymeric material. The knit stiffener from the distal section may extend into the proximal section. The braid may be formed from a single wire or multiple wires and may comprise more than one material. The coil may be formed from a helically wound wire, having a circular or rectangular cross-section (i.e., ribbon), for example. As shown in FIG. 5, the proximal segment 106 may include a braid 210 interposed between an inner proximal liner 212 and an outer proximal cover 214. As shown in FIG. 6, a coil 216 may also be interposed between the inner liner 212 and the outer cover 214.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What we claim is:
1. A method for manufacturing a catheter shaft, the method comprising:
   forming an inner polymeric tubular member;
   knitting an intermediate member from a single strand of wire;

disposing the intermediate member over the inner tubular member; and disposing an outer tubular member over the intermediate member and the inner tubular member.

2. The method of claim 1, wherein the intermediate member is formed of a plurality of knit loops.

3. The method of claim 2, wherein the single strand forms a plurality of up loops and a plurality of down loops.

4. The method of claim 3, wherein the plurality of up loops interlock with the plurality of down loops of the single strand.

5. The method of claim 2, wherein the knit member is tightly knitted such that it is generally not radially expandable.

6. The method of claim 1, wherein the intermediate member comprises a metal alloy.

7. The method of claim 1, wherein the intermediate member comprises a non-metallic material.

8. The method of claim 1, wherein the inner tubular member and the outer tubular member are in a coaxial relationship with the knit member.

9. The method of claim 1, wherein the outer tubular member is heat-shrunk over the intermediate member and the inner tubular member.

10. The method of claim 1, wherein the outer tubular member is extruded over the intermediate member and the inner tubular member.

11. A method for manufacturing a multi-layered catheter shaft having a proximal end, a distal end, and a passageway defining a distal end disposed between the proximal end and the distal end, the method comprising:

forming an inner polymeric tubular member;

knitting an intermediate member from a single wire to form a plurality of up loops interlocking with a plurality of down loops;

disposing the intermediate member over the inner tubular member; and disposing an outer tubular member over the intermediate member and the inner tubular member;

wherein the distal end of the catheter shaft is more flexible than the proximal end.

12. The method of claim 11, wherein the intermediate member comprises a metal alloy.

13. The method of claim 11, wherein the intermediate member comprises a non-metallic material.

14. The method of claim 11, wherein the knit member is tightly knitted such that it is generally not radially expandable.

15. A method for manufacturing a catheter shaft having a proximal end, a distal end, and a passageway defining a distal end disposed between the proximal end and the distal end, the method comprising:

forming an inner polymeric tubular member having a proximal end and a distal end;

knitting an intermediate tubular member from a single wire to form a plurality of up loops interlocking with a plurality of down loops;

disposing the intermediate tubular member over a distal portion of the inner tubular member;

disposing a stiffening member over a proximal portion of the inner tubular member; and disposing an outer tubular member over the intermediate tubular member, the stiffening member, and the inner tubular member;

wherein the distal end of the catheter shaft is more flexible than the proximal end.

16. The method of claim 15, wherein the stiffening member comprises a helically wound coil.

17. The method of claim 15, wherein the stiffening member comprises a braided member.

18. The method of claim 15, wherein the stiffening member comprises a metal alloy.

19. The method of claim 15, wherein the knit member is tightly knitted such that it is generally not radially expandable.

* * * * *